United States Patent [19]

Kleesattel et al.

[11] Patent Number: 4,490,114
[45] Date of Patent: Dec. 25, 1984

[54] ULTRASONICALLY DRIVEN LOW-SPEED ROTARY MOTOR

[75] Inventors: Claus Kleesattel, Rego Park; George E. Warrin, Merrick, both of N.Y.

[73] Assignee: Cooper LaserSonics, Inc., Santa Clara, Calif.

[21] Appl. No.: 113,984

[22] Filed: Jan. 21, 1980

[51] Int. Cl.³ ............................................. A61C 1/02
[52] U.S. Cl. .................................... 433/105; 433/119; 433/125; 74/1 SS
[58] Field of Search ............... 433/119, 125, 105, 103, 433/114; 51/59 SS; 310/26; 318/118; 128/24 A; 74/1 SS, 88, 111, 126, 128

[56] References Cited

U.S. PATENT DOCUMENTS

| | | | |
|---|---|---|---|
| 2,990,616 | 7/1961 | Balamuth et al. | 51/59 SS |
| 3,058,218 | 10/1962 | Kleesattle et al. | 433/131 |
| 3,139,543 | 6/1964 | Balamuth et al. | 51/317 |
| 3,254,402 | 6/1966 | Balamuth et al. | 228/110 |
| 3,848,336 | 11/1974 | Copeland | 433/105 |

*Primary Examiner*—John J. Wilson

*Attorney, Agent, or Firm*—Vorys, Sater, Seymour and Pease

[57] ABSTRACT

A device for rotating a member at relatively low rotational speeds is particularly useful for rotating a brush-type tooth polisher on an insert for an ultrasonic dental prophylaxis unit. The device comprises a vibrator which ultrasonically vibrates longitudinally and has a driving tip end portion which converts the longitudinal vibrations into elliptical motion. The elliptically moving driving tip tangentially engages at least one rotatable roller during an arc of the elliptical motion to rotate the roller. A speed reduction device couples the roller to a rotary polisher to rotate the polisher at a reduced speed. Preferably, the speed reduction device also isolates the axial and radial thrust applied, in use, to the polisher from the roller which receives some radial thrust from the vibrator. This reduces the bearing requirements for the polisher and roller. Also preferably, the roller, speed reduction and polisher elements are assembled as a unit separable from the vibrator for ready replacement.

11 Claims, 5 Drawing Figures

ULTRASONICALLY DRIVEN LOW-SPEED ROTARY MOTOR

BACKGROUND OF THE INVENTION

The invention relates to an ultrasonically driven, rotary device and, more particularly, a rotary dental polisher device.

One of the most widely accepted new dental instruments of recent years is the ultrasonic dental prophylaxis device. Such devices have a power unit which converts AC line-frequency electrical power into higher frequencies and a flexible cable which carries the higher frequency power to a handheld, tubular housing. An insert for the device has a sleeve for releasably connecting the insert to the housing and for supporting a vibrator. One end of the vibrator projects into the housing and is a magnetostrictive or other transducer device responsive to the higher frequency electrical power in the housing for producing longitudinal ultrasonic vibrations in the vibrator. The other end of the vibrator is the dental tool. The two ends of the vibrator are usually connected by a connecting body which, by a reduction in diameter or change in acoustic properties, amplifies the ultrasonic vibrations at the tool. The whole vibrator is also an integral multiple of one-half the wavelength of the ultrasonic vibrations in the vibrator to be resonant for maximum vibration and to have at least one node of ultrasonic vibration. The sleeve is usually arranged to support the vibrator at the node to avoid damping the vibrations.

The tool end of the vibrator has at least one bend which converts the longitudinal ultrasonic vibrations in the vibrator into ultrasonic elliptical motion at the tool end as described in the assignee's U.S. Pat. No. 2,990,616. The elliptical motion of the tool is then used to dislodge ultrasonically calculus, plaque and other matter adhered to teeth, particularly along the gum line. Removing calculus and plaque from teeth by hand is well known for the periodontal and hygienic treatment of teeth, and the ultrasonic dental prophyalaxis unit provides similar treatment with the improvement and assistance of ultrasonic vibrations.

In addition to removing calculus and plaque, however, teeth often require polishing or abrasive brushing to remove stains and otherwise clean broader areas of the teeth more rapidly. Such polishing is generally done with a relatively low-speed rotary rubber cup or brush and a polishing compound. Periodontists and hygienists have thus required two pieces of equipment: the ultrasonic dental prophylaxis device and a rotary polisher.

Rotary polishers have, until now, generally been driven by dental drilling equipment, but the very high rotational speeds (on the order of $10^5$ rpm) of modern high speed air turbine dental drills, while desirable for dental drilling, are greatly in excess of the rotational speeds suitable for the rotary brushing or polishing of teeth. One limitation on the speeds of such rotary polishing, for example, is retaining the polishing compound on the rotating brush. For this, rotational speeds on the order of $10^2$ to $10^3$ rpm are desired. If the more recent air turbine drive is thus to be used for rotary polishing, an expensive speed reduction device must be provided to achieve the much lower rotary polishing speeds, and an air power source also must be provided.

Alternatively, the old-fashioned, variable-speed, electrical, belt-driven dental-drilling apparatus may be used, but such devices with their large, multi-arm belt structures are particularly intimidating to patients. In addition, three pieces of equipment and two power supplies are then required for a full dental operatory: the electric ultrasonic prophylaxis unit for removing calculus and plaque, the high-speed turbine drill and air power supply, and the electric belt unit for polishing.

There has thus been for some years a desire to consolidate dental drilling, polishing and ultrasonic cleaning devices for economic and psycholological advantage. This desire, however, has so far led only to suggestions of combining the rotary drilling and polishing functions with the disadvantages just described, or to combining the ultrasonic prophylaxis and high-speed rotary drilling functions as described in the assignee's U.S. Pat. No. 3,058,218. This patent discloses a way of rotating a drill at high speeds through longitudinal ultrasonic vibrations. The longitudinal ultrasonic vibrations are produced at one end of a resonant vibrator insert plugged into a housing with energizing means and converted into elliptical motion at the other end of the vibrator in the same way as described for the ultrasonic dental prophylaxis device. The elliptically-moving end of the vibrator tangentially engages a shaft, which is rotatably mounted in or adjacent to the vibrating tip during one arc of the ellipse. The high frequency of the ultrasonic vibrations, generally in a range of from 15 to 50 KHZ, however, rotates the shaft at correspondingly high speeds of from 45,000 to 360,000 rpm in the examples in the patent. Such speeds are greatly in excess of those suitable for rotary polishing, at least because the polishing compound cannot be retained on the polisher. Thus, even though the patent initially suggests using the ultrasonically driven rotary device for "abrading and polishing operations", such operations must be considered grinding-type polishing and not the brushing-type polishing for cleaning teeth considered here. This is further confirmed by the patent's consistent emphasis of high rotational speeds, as opposed to the low speeds desired for polishing.

The patent also discloses only rotating the drill shaft directly from the elliptically-moving end of the vibrator. As the elliptical motion tangentially engages the shaft during one arc of the ellipse to rotate the shaft unidirectionally it must impart some radial thrust to the shaft to achieve the tangential driving engagement. In use, however, the rotated polisher tool shaft or drill has some axial thrust applied to it. It has been found difficult, at least economically, to provide a bearing for a directly rotated element or elements as disclosed in the patent which will endure these radial and axial thrusts in the presence of ultrasonic vibrations. The relatively bulky and costly bearings necessary to try to accomodate the combined radial and axial thrusts also absorbed substantial power which could be preserved for the rotary output if the bearing loads could be reduced to reduce the required bearing strength and bulk. Thus, for these practical reasons, too, the device disclosed in the patent is not suitable for a rotary low-speed or brush-type polisher.

Rotating the drill shaft directly from the elliptically-moving end of the vibrator also required offsetting the drill shaft from the longitudinal axis of the vibrator to achieve the drill-rotating tangential engagement with the vibrator. Locating the rotated (drill) shaft on the axis of the vibrator, however, would make the device both easier to use and through proper design still further reduce the shaft bearing requirements by eliminating the torque exerted on the insert (and handpiece) by the axial forces.

SUMMARY OF THE INVENTION

It is therefore an object of the invention to provide a single device suitable for both ultrasonic dental prophylaxis treatment and the relatively low speed rotary polishing of teeth.

It is further an object of the invention to provide a device which rotates a member such as a polisher at relatively low rotational speeds through longitudinal ultrasonic vibrations.

To these ends, the invention provides a device which rotates a member at relatively low speeds through longitudinal ultrasonic vibrations. The device will be described in relation to its preferred embodiment of a rotary dental polisher, but is not limited to this preferred embodiment for dentistry.

As before described, ultrasonic dental prophylaxis devices having a power unit connected to a tubular, hand-held housing by a flexible cable are known. The preferred embodiment is an insert for plugging into the housing of such ultrasonic dental prophylaxis devices in place of the usual elliptically-moving dental tool insert for such devices and, more particularly, a rotary polisher head unit for such an insert. It can thus already be appreciated that the preferred embodiment provides an additional way of using the ultrasonic dental prophylaxis device for the rotary polishing of teeth. The electric prophylaxis device then replaces two pieces of equipment formerly required for modern dental treatment, and eliminates an air power supply if a turbine unit is replaced. In addition, the intimidating aspects of dental drilling apparatus can be entirely avoided by completely eliminating the drilling apparatus from a dental prophylaxis operatory where it had been used only for cleaning and polishing teeth. Two benefits from the preferred embodiment of the invention are thus readily apparent.

In the preferred embodiment, the insert comprises a sleeve which is plugged into the housing of an ultrasonic dental prophylaxis device. A vibrator is mounted within the sleeve with a transducer end projecting into the housing for producing longitudinal ultrasonic vibrations in the vibrator. The other end of the vibrator projects from the other end of the sleeve and converts the longitudinal ultrasonic vibrations into elliptical motion (which as used herein includes circular and other loop movements). A roller is supported from the sleeve for axial rotation adjacent the elliptically-moving end of the vibrator so that the vibrator tangentially engages the roller during an arc of the elliptical motion to rotate the roller unidirectionally. A speed reduction device connects the roller to a rotable member, which is a polisher in this embodiment, to rotate the polisher at a reduced speed suitable for polishing. Both the speed reduction device and the rotatable member (polisher) are also supported from the sleeve.

This arrangement provides two further benefits which are also features of the invention. Inasmuch as the end of the vibrator which engages the roller moves elliptically, it must impart some radial thrust to the roller to achieve the periodic tangential engagement which rotates the roller unidirectionally. This radial thrust on the roller must be taken up by the bearings which support the roller for rotation. When the polisher is in use, however, some pressure is applied between the rotating polisher and the tooth being polished which produces both axial and radial thrusts on the polisher. These thrusts must be taken up by the bearings which support the polisher. Bearings which accommodate axial and radial thrusts are known, but are relatively expensive and lossy are compared to bearings which principally accomodate radial or axial thrust alone. The speed reduction device in the preferred embodiment thus separates the roller from the polisher so that the less expensive axial and radial thrust bearings may be used on the polisher and roller, respectively. The speed reduction device thus both reduces the rotational speed and isolates the radical and axial thrusts. The radial and axial thrust isolation reduces the cost and bearing power losses of the bearings for independently supporting the roller and polisher shafts. Also, the speed reduction device can be used to put the polisher shaft on the longitudinal axis of the vibrator, so that the torque generated on the handpiece by the axial thrust applied to the polishing cup is eliminated.

The second further advantage of the preferred embodiment is that the roller, speed reduction device and polisher are all supported from the sleeve independently of the vibrator and thus can be assembled as a unit or head readily releasable from the insert. Different polisher units or heads having different speed reductions can thus be interchanged on a single vibrator to vary the operating characteristics of the device. In addition, the ultrasonic vibration from the vibrator tends to wear even the highest quality rotary bearings for the roller, whereas the ultrasonic vibrator has a very long useful life. Being able to replace a worn head unit without having to replace the vibrator is thus economically advantageous.

DESCRIPTION OF THE DRAWINGS

Preferred embodiments which are intended to illustrate but not to limit the invention will now be described with reference to drawings in which.

DESCRIPTION OF THE PREFERRED EMBODIMENTS

Figure 1:
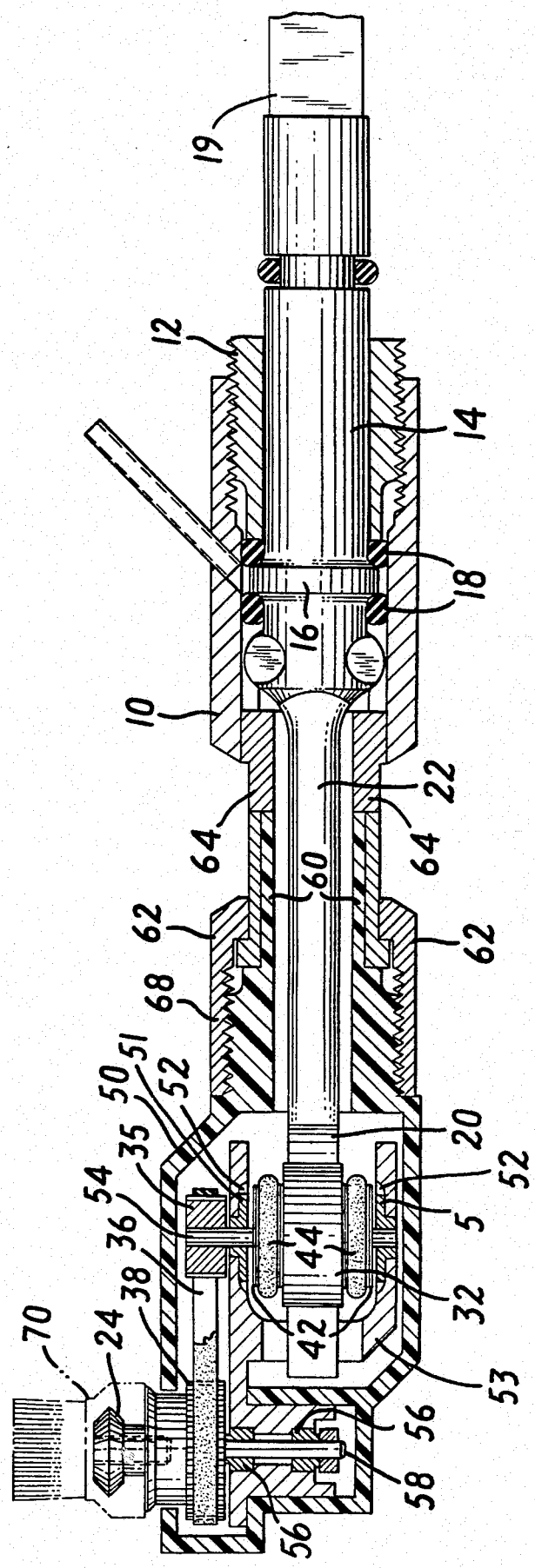
FIG. 1 is an enlarged elevation of one preferred embodiment, partly in section.
Figure 4:
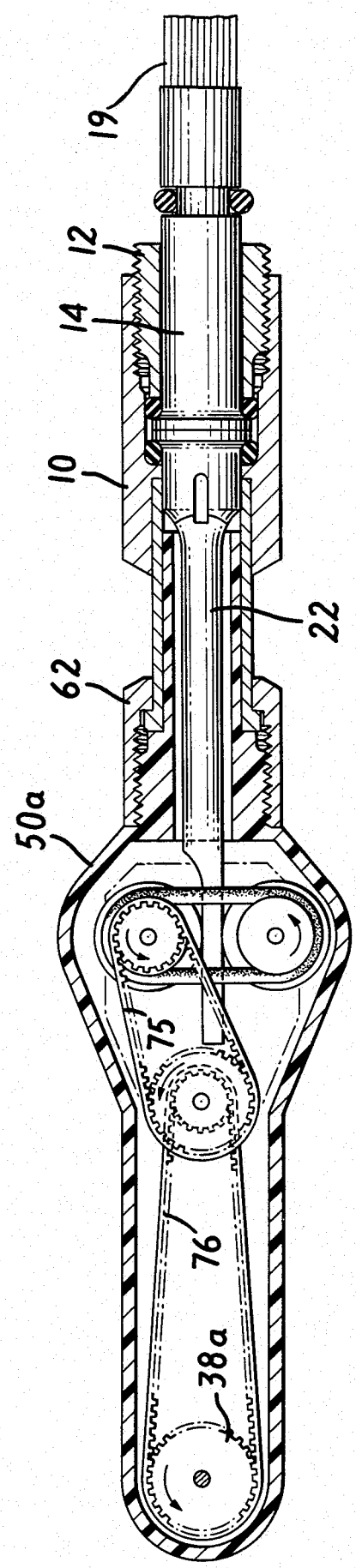
FIG. 4 is an enlarged bottom view of another preferred embodiment, partly in section.

The preferred embodiments shown in FIGS. 1 and 4 are inserts for an ultrasonic dental prophylaxis device (not shown). Such devices are well known to comprise a power unit which converts line AC electrical power into higher frequency electrical power which is supplied to a hand-held, tubular housing through a flexible cable. Cooling water is also usually provided from the power unit to the housing through the cable. Although such ultrasonic dental prophylaxis devices are sufficiently well known to require no further description, they are further described in the assignee's beforementioned U.S. Pat. No. 2,990,616.

The preferred embodiment shown in FIG. 1 has a composite sleeve structure 10 which is pluggable into the housing of the ultrasonic dental prophylaxis unit at a retainer end 12. A vibrator 14 is mounted in the sleeve at a flange 16 by a pair of resilient rings 18. One end of the vibrator projects from the retainer end 12 of the sleeve into the housing and comprises a magnetostrictive transducer 19 responsive to the higher frequency electric current in the housing to produce longitudinal ultrasonic vibrations in the vibrator. Again, this is sufficiently well known to require no further description, but is described in the beforementioned U.S. Pat. No. 2,990,616. The driving tip 20 end of the vibrator projects from the other end of the sleeve 10 and is connected to the transducer 19 by a connecting body 22 which may include a change in diameter such as to increase the amplitude of the longitudinal ultrasonic vibrations at the driving tip 20 of the vibrator, again in a manner so well known as to require no further description, but as described in another of the assignee's U.S. Pat. No. RE 25,033.

Figure 2:
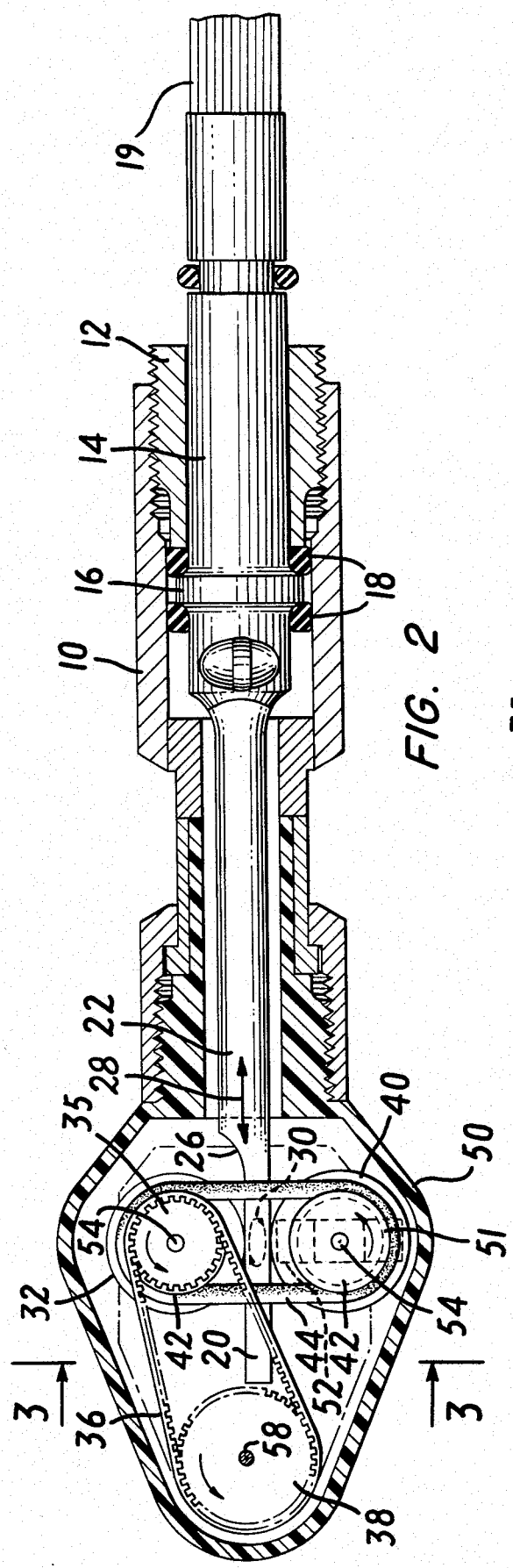
FIG. 2 is a bottom view of the embodiment shown in FIG. 1, partly in section.

FIG. 2 better shows the way in which the longitudinal ultrasonic vibrations in the vibrator 14 rotationally drive the polisher 70 (FIG. 1). The driving tip 20 end of the vibrator has an asymmetric change in cross section which, in this embodiment is an asymmetric step 26 at the driving end of the vibrator. As explained in the beforementioned U.S. Pat. No. 2,990,616, this converts the longitudinal ultrasonic vibrations indicated by arrow 28 into elliptical motion indicated by arrow 30 in the driving tip 20.

For greatest efficiency, the major axis of the ellipse is parallel to the vibrator axis with the minor axis only as large as needed to engage the vibrator end 20 with at least one roller 32 during the longitudinal movement in one direction and disengage it from said roller during longitudinal movement in the opposite direction sufficiently to rotate the roller unidirectionally. The longitudinal stroke of the ultrasonic vibrations is small, on the order of $10^{-3}$ inch ($10^{-3}$ cm), however; there is no visible clearance between the driving tip 20 and the roller 32 shown in the enlarged Figures, since the transverse movement is even much smaller.

Thus, as the driving tip 20 of the vibrator moves elliptically as shown by arrow 30, it engages the roller 32 tangentially during the upper arc of the ellipse as shown in FIG. 2 when it is moving to the right. The roller 32 is thus rotated counter clockwise. During the other, lower arc of the elliptical motion shown by arrow 30 in FIG. 2, the driving tip 20 is disengaged from the roller 32. The tangential engagements of the driving tip 20 and the roller 32 thus continually rotate the roller 32 unidirectionally counter clockwise.

Figure 2A:
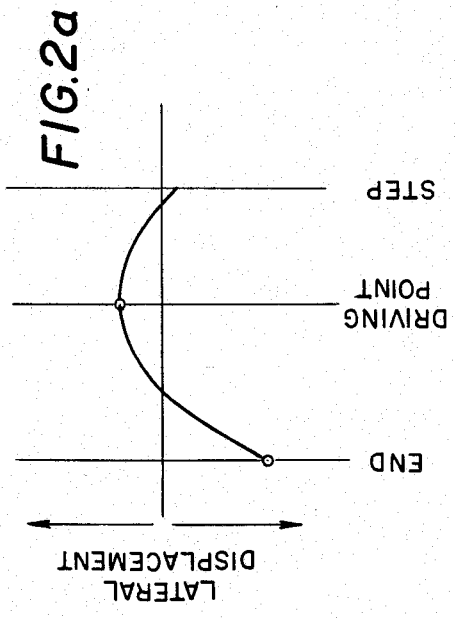
FIG. 2a is a diagram of the lateral displacement of a portion of the preferred embodiment shown in FIG. 1.

The elliptical motion indicated by arrow 30 which rotates the roller 32 is spaced from the free end of the driving tip 20 toward the body of the vibrator 14. The spacing from the end of the driving tip is one half the flexural wavelength introduced into the driving tip by the asymmetric step 26 to be at a loop (maximum) of the elliptical motion. Using the elliptical motion loop between the step 26 and the end of the driving tip provides several advantages over using the loop at the free end of the driving tip as disclosed in several embodiments in U.S. Pat. No. 3,058,218. For one, a broader area of contact with the roller is provided to reduce wear. For another, slight longitudinal misalignments between the roller and driving tip merely shift the driving contact to less-than-maximum lateral motion along the driving tip, but the reduction from maximum is less than would result at the free end of the driving tip because of the smaller gradient in the lateral displacement as shown in FIG. 2a.

The ultrasonic vibration is at a frequency of from 15 to 50 KHZ, and preferably about 25 KHZ, the ultrasonic frequency at which commercial ultrasonic dental prophylaxis devices commonly operate. Inasmuch as the rotational speed is proportional to the product of amplitude and frequency, the high frequency of the vibration-produced successive engagements between the driving tip 20 and roller 32, even over the limited stroke of the arc during which the driving tip tangentially engages the roller, rotates the roller at an appreciable rotational speed on the order of $10^3$ rpm. Such rotational speeds are, however, still too fast for retaining polishing compound on the polisher 70 (FIG. 1), but cannot be conveniently reduced further without unreasonably increasing the diameter of the roller. Direct connection of the polisher to the roller is thus unsuitable for a practical rotary polisher.

The roller 32, however, is connected to a toothed wheel 35 of a speed-reducing belt drive. The speed-reducing belt drive device further includes a toothed belt 36 which extends from the roller-driven wheel 35 to a larger toothed wheel 38. The larger wheel 38 is connected to the polisher to rotate the polisher at a reduced speed of from about 800 to 2,000 rpm. Especially at the lower end of such speed range, polishing compound is retained on a polisher 70 so that a practical rotary tooth polisher has been devised. Using the toothed belt in the speed reduction device also allows the belt to be slack; this reduces power losses in the speed reduction device as compared to a friction belt drive.

Figure 3:
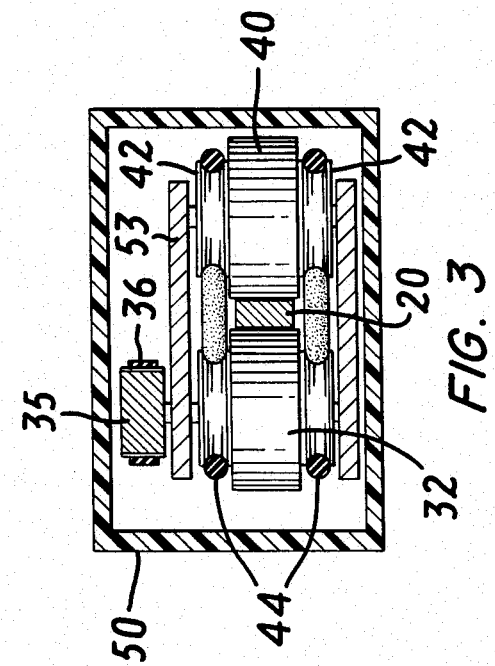
FIG. 3 is an end view of the embodiment shown in FIGS. 1 and 2, partly in section.

As further shown in FIG. 2, to increase the torque and thus the output power of the device a second roller 40 is preferably on the opposite side of the driving tip 20 from the roller 32 for tangential engagement with the driving tip during the opposite arc of the elliptical motion. Both directions of the longitudinal ultrasonic vibration are thus used alternately to rotate a roller. Upper and lower grooves 42 (FIG. 3) on each roller 32, 40 and resilient, taut belts 44 provide both the required static force between the driving tip and the rollers, and equalize the rotational speeds of the two rollers. The two rollers 32, 40 thus drive the speed reduction device of belt and wheels 35, 36 and 38 to rotate the polisher 70 more efficiently, because of the greatly reduced bearing losses, and produce a larger power output.

More importantly, however, the yieldable belts provide balanced forces urging the rollers into driving contact with the driving tip 20 and, in combination with the roller support arrangement, absorb the radial drive-engaging thrusts on the rollers while at the same time taking away the radial loading forces from the bearings: (which are necessary for the friction drive), whereby the bearing losses are greatly reduced, making it possible to use tiny, inexpensive sleeve bearings instead of bulky and costly ball bearings.

Returning to FIG. 1, the way in which a housing 50 supports the various rotary elements from the sleeve 10 is shown. Upper and lower sleeve bearings 51 slide perpendicularly to the driving tip 20 surfaces in slots 52 in a frame 53 of the housing 50 and support upper and lower portions of two respective pins 54 for the rollers 32, 40. A separate bearing 56 supports a shaft 58 for the polisher 70 and speed reduction wheel 38 on the frame 53. All the rotational elements are thus supported on the frame 53.

The housing 50 has a support portion 60 which snugly fits into the sleeve 10. A collar 62 rotationally slides about the sleeve 10 that has a dog 64 on one end which engages a notch on the support portion 60 of housing 50. The opposite end 68 of the collar 62 has internal threads which engage matching external threads on the housing 50 to releasably hold the housing 50 on the sleeve 10. Having all the rotary elements on the frame 53 within the housing 50 thus provides a replaceable polisher head unit for the insert.

The speed reduction device also serves to isolate the axial and radial thrusts from the roller bearings 51 from the separate polisher bearings 56. There is, however, substantially no axial thrust on the bearings 52. Some axial thrust, however, is necessarily applied to the polisher 70 (FIG. 1) in use. The separate bearings 56 for the polisher are thus designed to accommodate substantially only axial thrust and the relatively low frequency of radial thrust developed by using the polisher. The speed reduction device between the roller and polisher thus separates the forces that come from the polisher 70, when doing work, from the roller assembly. The isolation of the polisher bearings 56 makes it possible to locate the axle 58 on the handpiece center line. The speed reduction device thus serves a thrust isolation function in addition to its speed reducing function.

With practically no thrusts on the bearings 51 for the rollers 32, 40, the bearings 51 can be simple, inexpensive sleeve bearings. The bearings 51 are mounted in the slots 52 for sliding movement toward and away from the driving tip. The belts 44 are elastic to urge the rollers against the driving tip.

The bearings 51 can be inexpensively designed, since they have essentially only a roller-aligning function. The ultrasonic frequency of the radial impacts may still tend to wear the bearings 51. The vibrator 14, however, has a very long useful life, but is costly. The collar 60 which releases the rotary elements in housing 50 or head unit from the sleeve and vibrator portion of the insert is thus especially useful for replacing the rotary elements when worn without having to replace the sleeve and vibrator.

In addition to its speed-reducing and thrust isolation functions, the speed reduction device also serves as a way of putting the shaft 58 of the polisher on the longitudinal axis of the vibrator. This makes the device easier to manipulate.

FIG. 1 shows, in phantom, a push-on rubber cup style polisher 70, which can snap over the hub 24 end of shaft 58. The polisher elements can thus be interchanged. If, however, a different rotational speed for the polisher is required, the collar 62 can release the housing 50 or head unit so that a housing unit having a different speed reduction device can be substituted. Again, therefore, having all the rotary elements assembled as a unit on the housing 50 which is readily releasable from the remainder of the insert is useful.

FIG. 4 shows an alternative housing 50a which may be substituted in the way just described for the housing unit 50 shown in FIG. 1. In the housing unit 50a, there are two speed-reducing, wheel and belt drive units 75, 76 in the rotary drive train to a polisher drive wheel 38a.

The preferred embodiments now described illustrate our invention. Other alternative embodiments, improvements, and variations of the invention are contemplated as being within the scope of the following claims. One example of such an alternative is a contra-angle polisher.

We claim:

1. An insert for a device having a housing with means for exciting longitudinal ultrasonic vibrations, the insert comprising:
   a sleeve for plugging the insert into the housing;
   a vibrator supported in the sleeve, having a transducer at one end projecting toward the housing and responsive thereto for producing longitudinal ultrasonic vibrations in the vibrator, and having driving tip means at the other end for converting the longitudinal ultrasonic vibrations into elliptical motion;
   at least one roller rotatably supported from the sleeve adjacent the driving tip means for axial rotation, the driving tip means tangentially engaging the roller during an arc of the elliptical motion of the driving tip means for unidirectionally rotation the roller;
   tension means for providing a loading force between the roller and the driving tip;
   a member rotatably supported from the sleeve; and
   rotational speed reduction means coupling the roller to the member for rotating the member at a reduced rotational speed.

2. An insert as in claim 1, wherein the rotational speed reduction means further comprises means for isolating the roller from the forces acting on the member when the latter is in contact with a solid surface.

3. An insert as in claim 1 wherein the sleeve comprises a frame for supporting the roller, member and speed reduction means as a unit; and means releasably connecting the frame unit to the sleeve for replacement thereof.

4. An insert as in claim 1, 2 or 3; and further comprising rotational bearing means supporting the roller from the sleeve for movement generally toward and away from the driving tip means.

5. An insert as in claim 1, 2 or 3; and further comprising a second axially rotatable roller supported from the sleeve on an opposite side of the driving tip means from the first-mentioned roller for rotation by tangential engagement during an opposite arc of the elliptical motion of the driving tip means, and connecting means for rotationally connecting the first and second rollers.

6. An insert as in claim 5 wherein the tension means comprise two elastic belts extending respectively around opposite ends of each roller.

7. An insert as in claim 1, 2, or 3, wherein the rotational axis of the roller is offset from the longitudinal axis of the vibrator and wherein the rotational speed reduction means further comprises means for rotating the member with the rotational axis of the member intersecting the longitudinal axis of the vibrator.

8. An insert as in claim 1, 2, or 3, wherein the driving tip means has a free end and wherein the driving tip means tangentially engages the roller approximately at a loop of the elliptical motion spaced toward the transducer means from the free end of the driving tip means.

9. A low speed rotary polisher insert for an ultrasonic device having a housing with means for inducing longitudinal ultrasonic vibrations, the insert comprising:
   a sleeve for plugging the insert into the housing;
   a vibrator supported in the sleeve, having a transducer at one end projecting toward the housing and responsive thereto for producing longitudinal ultrasonic vibrations in the vibrator, and having driving tip means at the other end for converting the longitudinal ultrasonic vibrations into elliptical motion;

a frame;

means for releasably connecting the frame to the sleeve;

a pair of rollers including bearing means supporting the rollers on the frame for axial rotation, the rollers being on opposite sides of the driving tip means for tangential engagement thereby during opposite arcs of the elliptical motion thereof to rotate the rollers axially;

means for urging the rollers against the driving tip and for simultaneous rotational coupling of the rollers;

a polisher rotatably projecting from the frame; and speed reduction means on the frame and connecting at least one of the rollers to the polisher for rotating the polisher at a reduced speed and for isolating the radial thrust applied to the rollers by the elliptical motion of the driving tip means from the polisher.

10. An insert as in claim 9 wherein the roller bearing means support at least one of the rollers in a slot for movement perpendicular to the driving tip means, and wherein the means for rotationally coupling the rollers comprise two elastic belts extending respectively around opposite ends of each roller for yieldably urging the rollers and driving tip means together with balanced forces.

11. For use in an ultrasonic device having a projecting vibrator portion moving elliptically, a polisher head unit comprising:

a frame;

means for releasably connecting the frame to the ultrasonic device with the projecting, elliptically moving vibrator portion extending toward the frame;

at least one roller having an axis of rotation generally normal to the vibrator portion, loading means for urging the roller against the vibrator portion and bearing means supporting the roller on the frame adjacent the projecting vibrator portion for tangential engagement thereby during an arc of the elliptical motion thereof to rotate the roller unidirectionally;

a polisher rotatably projecting from the frame; and speed reduction means on the frame and connecting the roller to the polisher for rotating the polisher at a reduced speed and for isolating thrusts applied to the polisher and bearing means from each other.

* * * * *